United States Patent [19]
Schneider et al.

[11] Patent Number: 5,466,457
[45] Date of Patent: Nov. 14, 1995

[54] COSMETIC STICKS

[75] Inventors: Günther Schneider, Hamburg; Manfred Klier, Aumühle; Marta Aul, Buchholz, all of Germany; Stephan Teichmann, Tokyo, Japan

[73] Assignee: Beiersdorf Aktiengesellschaft, Hamburg, Germany

[21] Appl. No.: 203,085

[22] Filed: Feb. 28, 1994

[30] Foreign Application Priority Data

Mar. 1, 1993 [DE] Germany .......................... 43 06 068.4

[51] Int. Cl.⁶ .............................. A61K 7/00; A61K 7/025
[52] U.S. Cl. ......................... 424/401; 424/78.03; 424/64; 424/DIG. 5; 514/787; 514/953; 514/785
[58] Field of Search .............................. 424/401, DIG. 5, 424/78.03, 69, 63, 64

[56] References Cited

U.S. PATENT DOCUMENTS

| | | | |
|---|---|---|---|
| 4,291,018 | 9/1981 | Oeda et al. | 424/DIG. 5 |
| 4,919,934 | 4/1990 | Deckner et al. | 424/401 |

FOREIGN PATENT DOCUMENTS

| | | |
|---|---|---|
| 2079601 | 1/1982 | United Kingdom . |
| 9304658 | 3/1993 | WIPO . |

OTHER PUBLICATIONS

Derwent AN 90–073603 & SU–A–1 503 817.
Derwent AN 93–157613 & SU–A–1 734 748.
Chemical Abstract, vol. 100, No. 2, 1984, 12459c & JP–A–58 162 510.
Chemical Abstract, vol. 100, No. 24, 1984, 197641x.

*Primary Examiner*—Raj Bawa
*Attorney, Agent, or Firm*—Sprung Horn Kramer & Woods

[57] ABSTRACT

A uniform lipstick molded of a composition by weight consisting of 0.5 to 50% beeswax, 0.5 to 50% of at least one ester of a saturated carboxylic acid and a saturated alcohol, the acid having 10–19 carbon atoms and the alcohol 14–40 carbon atoms, or the acid having 20–40 carbon atoms and the alcohol having 35–40 carbon atoms, 0.1 to 20% of water, and optionally other lipids and customary auxiliaries and additives, the composition being substantially free of mineral fatty components and paraffins.

10 Claims, No Drawings

COSMETIC STICKS

DESCRIPTION

The present inventions relates to cosmetic sticks, in particular lipsticks, preferably lip care sticks, and to compositions and processes for the preparation of cosmetic sticks.

The horny cell layer of the lips' skin is only extremely thin. There are no perspiratory glands on the lips, and only few sebaceous glands. The skin of the lips is therefore virtually free from lipids and is prone to drying out, in particular in cold and dry weather. Small cracks may form in the skin, and the susceptibility of the lips to chemical, physical and microbial factors (for example foodstuffs, sunlight, Herpes simplex viruses) increases.

It is the purpose of lip care sticks to prevent this from happening. These products usually contain a large amount of waxes and fatty components which form a covering layer on the lips after application.

Additional active substances which enhance the care or the protection of the lips can be incorporated into the preparations for lip care sticks, for example vitamins, moisturizers, light stabilizers, covering pigments and the like.

The dermis of the lips is provided with papillae which are well supplied with blood and which reach up to close below the surface of the lips. This is why the lips are red and more or less distinct with regard to colour from the remaining facial skin, depending on the skin colour of the person in question. Using suitable cosmetics, matching the lip colour with the type of the person is a stylistic element of decorative cosmetics.

Products of this nature are decorative lipsticks into which a very wide range of pigments can be incorporated. These sticks, too, contain large amounts of waxes and fatty components which form a covering lipid layer on the lips after application.

However, the purpose of this layer is not primarily to protect the skin of the lips against drying out. The lipid layer is used in this case as a base for the incorporated pigments which adheres to the lips; the pigments themselves cannot be applied to the lips without such a base, for various reasons.

It is also possible to combine the characteristics of the nourishing and the decorative lipsticks with each other, i.e. to incorporate nourishing or protecting substances into decorative lipsticks.

From the technological point of view, virtually all lipsticks are water-free lipid mixtures composed of solid or semisolid waxes and liquid oils, the lipstick base being ultra pure liquid paraffins and ultra pure paraffin waxes.

The ideal profile of requirements includes smooth application of the lipsticks without substantial friction. Moreover, a lipstick should leave a non-greasy, dull or sticky lipid film even when pressed on slightly, which should nevertheless adhere well. This lipid film is intended to make the lips smooth and soft.

Moreover, a lipstick must also meet the requirements of being resistant to breaking and to temperature, and it must not oil.

Conventional basic materials of the prior art are:

(1) liquid oils (for example liquid paraffins, castor oil, isopropyl myristate)

(2) semi-solid components (for example white petroleum jelly, lanolin)

(3) solid components (for example beeswax, ceresin and microcrystalline waxes or ozocerite)

(4) waxes having a high melting point (for example carnauba wax, candelilla wax).

Lipsticks of the prior art which contain paraffins and beeswax are described in "Kosmetik, Entwicklung Herstellung und Anwendung kosmetischer Mittel" [Cosmetology, development, preparation and use of cosmetics] , p. 105, Editor: W. Umbach, Georg Thieme Verlag, Stuttgart—New York, 1988.

However, the prior art has a series of disadvantages. This includes the fact that water-soluble active substances are frequently not fat-soluble enough to be incorporated to a substantial extent into the cosmetic bases. On the other hand, a certain water content would be desired to increase the compatibility of the cosmetic stick with the human skin.

DBP 2,335,549 discloses a process for the preparation of a cosmetic stick based on a W/O emulsion. According to this teaching, a gel is prepared from a polyhydroxy compound and a non-ionic, surface-active compound, this gel is mixed with a cosmetic base, and a water content is then emulsified into the mixture.

However, this process does not allow sticks to be prepared which meet the universal requirements demanded of a cosmetic stick.

A further disadvantage is that liquid paraffins and paraffin waxes were up to the present point in time indispensable components of lipsticks. Even though they are raw materials which can be obtained in good quality and sticks which have useful properties can be formulated with their aid, the use properties of such cosmetic sticks are however limited. Moreover, paraffins are valuable basic materials whose occurrence/supply on the earth is limited. Modern production tends to use renewable raw materials, that is, for example, vegetable waxes or oils, in the field of cosmetics.

It has however hitherto been impossible to design a cosmetic stick based on the known vegetable waxes, fats or oils or chemically modified vegetable waxes, fats or oils. It was therefore a further object of the present invention to provide a basis for cosmetic sticks, in particular lipsticks, where mineral oils can be dispensed with and instead of these vegetable or, if appropriate, animal fatty components or their chemically modified variants can be used as a base.

It was surprising and could not have been predicted that compositions for cosmetic sticks containing:

(a) beeswax, (b) esters of (ba) a saturated carboxylic acid having 10–19 carbon atoms and (bb) a saturated alcohol having 14–40 carbon atoms, (c) optionally water and (d) other lipids and/or customary auxiliaries and additives, and compositions for cosmetic sticks containing (a) beeswax, (b) esters of (ba) a saturated carboxylic acid having 20–40 carbon atoms and (bb) a saturated alcohol having 35–40 carbon atoms, (c) optionally water and (d) other lipids and/or customary auxiliaries and additives, would result in lipsticks which have all the required characteristics that would overcome the disadvantages of the prior art.

Using the compositions according to the invention it is possible, in particular, to obtain emulsion lipsticks or emulsion lip care sticks and to dispense completely with an addition of mineral fatty components or paraffins, irrespective of whether water is to be incorporated or not.

Moreover, the present invention allows emulsion lipsticks to be provided which do not have the disadvantages of the prior art.

The esters (A)–(J) are very particularly advantageous:

(A) Hexacosanyl palmitate (synonym: hexacosanyl hexadecanoate), of the formula $$H_3C-(CH_2)_{25}-O-\underset{O}{\underset{\|}{C}}-(CH_2)_{14}-CH_3$$

(B) Octacosanyl palmitate (synonym: octacosanyl hexadecanoate), of the formula $$H_3C-(CH_2)_{27}-O-\underset{O}{\underset{\|}{C}}-(CH_2)_{14}-CH_3$$

(C) Triacontanyl palmitate (synonym: triacontanyl hexadecanoate), of the formula $$H_3C-(CH_2)_{29}-O-\underset{O}{\underset{\|}{C}}-(CH_2)_{14}-CH_3$$

(D) Dotriacontanyl palmitate (synonym: dotriacontanyl hexadecanoate), of the formula $$H_3C-(CH_2)_{31}-O-\underset{O}{\underset{\|}{C}}-(CH_2)_{14}-CH_3$$

(E) Tetratriacontanyl palmitate (synonym: tetratriacontanyl hexadecanoate), of the formula $$H_3C-(CH_2)_{33}-O-\underset{O}{\underset{\|}{C}}-(CH_2)_{14}-CH_3$$

(F) Hexacosanyl stearate (synonym: hexacosanyl octadecanoate), of the formula $$H_3C-(CH_2)_{25}-O-\underset{O}{\underset{\|}{C}}-(CH_2)_{16}-CH_3$$

(G) Octacosanyl stearate (synonym: octacosanyl octadecanoate), of the formula $$H_3C-(CH_2)_{27}-O-\underset{O}{\underset{\|}{C}}-(CH_2)_{16}-CH_3$$

(H) Triacontanyl stearate (synonym: triacontanyl octadecanoate), of the formula $$H_3C-(CH_2)_{29}-O-\underset{O}{\underset{\|}{C}}-(CH_2)_{16}-CH_3$$

(I) Dotriacontanyl stearate (synonym: dotriacontanyl octadecanoate), of the formula $$H_3C-(CH_2)_{31}-O-\underset{O}{\underset{\|}{C}}-(CH_2)_{16}-CH_3$$

(J) Tetratriacontanyl stearate (synonym: tetratriacontanyl octadecanoate), of the formula $$H_3C-(CH_2)_{33}-O-\underset{O}{\underset{\|}{C}}-(CH_2)_{16}-CH_3$$

Octacosanyl stearate is the preferred ester.

The esters were synthesized and provided by the company Koster Keunen Holland B.V.

Due to the preparation process, the esters may contain certain unhazardous by-products and unreactive starting substances. It is advantageous to employ commercially available goods whose ester content is at least 80% by weight based on the total weight of the product.

Beeswax (synonyms are: cera flava (yellowish) and cera alba (white), or in agreement with CTFA: beeswax) is mainly composed of myristyl palmitoate, cerotic acid, melissic acid, higher alcohols and hydrocarbons. More recent investigations suggest that beeswax is composed of a homologous series of mostly $C_{35}$- to $C_{54}$-alkyl hexadecanoates ("Lexikon der Hilfsstoffe für Pharmazie, Kosmetik und angrenzende Gebiete" [Encyclopedia of auxiliaries for pharmacology, cosmetology and adjacent fields], H. P. Fiedler, 3rd Ed., 1989, Editio Cantor Aulendorf, and sources and cross-references cited therein under the headword "beeswax").

Beeswax has been used since ancient times as an important cosmetic ingredient, in particular for creams and ointment preparations, but also for cosmetic sticks. A lipstick of the prior art contains 4.0% by weight of beeswax.

Excessive proportions of beeswax have hitherto always resulted in matt and granular cosmetic sticks. The stability of such sticks, too, always left something to be desired. It has always been a considerable disadvantage that beeswax-based cosmetic sticks were inelegant from the cosmetic point of view.

As is known, however, a certain amount of beeswax imparts strength to lipsticks and causes good adhesion of the lipstick composition to the lips ("Kosmetik, Entwicklung, Herstellung und Anwendung kosmetischer Mittel" [Cosmetology, development, preparation and application of cosmetics], p. 104 and throughout, W. Umbach (Editor), 1988, Georg Thieme Verlag, Stuttgart). Even so, beeswax is not an obligatory ingredient of cosmetic sticks, probably because of the abovementioned reasons.

The cosmetic sticks according to the invention advantageously contain

| | |
|---|---|
| 0.5–50% by weight | of beeswax, |
| 0.5–50% by weight | of an ester of a saturated carboxylic acid having 10–19 |

| | -continued |
|---|---|
| | carbon atoms and a saturated alcohol having 14–40 carbon atoms, and |
| 0.1–20% by weight in particular | of water, |
| 2.0–20% by weight | of beeswax, |
| 2.0–25% by weight | of an ester of a saturated carboxylic acid having 10–19 carbon atoms and a saturated alcohol having 14–40 carbon atoms, and |
| 1.0–10% by weight preferably | of water, |
| 3.0–10% by weight | of beeswax, |
| 5.0–20% by weight | of an ester of a saturated carboxylic acid having 10–19 carbon atoms and a saturated alcohol having 14–40 carbon atoms, and |
| 1.0–5% by weight very particularly preferably | of water, |
| 4.0–6.0% by weight | of beeswax, |
| 15.0–18.0% by weight | of an ester of a saturated carboxylic acid having 10–19 carbon atoms and a saturated alcohol having 14–40 carbon atoms, and |
| 2.0–3.0% by weight | of water. |

It is preferred to select the ratio of beeswax and one or more esters of a saturated carboxylic acid having 10–19 carbon atoms and a saturated alcohol having 14–40 carbon atoms, in particular the esters (A) to (J), particularly preferably octacosanyl stearate, in a ratio of approximately 1:1 to approximately 1:5, in particular approximately 1:3.

The cosmetic sticks according to the invention furthermore advantageously contain

| 0.5–50% by weight | of beeswax, |
|---|---|
| 0.5–50% by weight | of an ester of a saturated carboxylic acid having 20–40 carbon atoms and a saturated alcohol having 35–40 carbon atoms, and |
| 0.1–20% by weight in particular | of water, |
| 2.0–20% by weight | of beeswax, |
| 2.0–25% by weight | of an ester of a saturated carboxylic acid having 20–40 carbon atoms and a saturated alcohol having 35–40 carbon atoms, and |
| 1.0–10% by weight preferably | of water, |
| 3.0–10% by weight | of beeswax, |
| 5.0–20% by weight | of an ester of a saturated carboxylic acid having 20–40 carbon atoms and a saturated alcohol having 35–40 carbon atoms, and |
| 1.0–5% by weight very particularly preferably | of water, |
| 4.0–6.0% by weight | of beeswax, |
| 15.0–18.0% by weight | of an ester of a saturated carboxylic acid having 20–40 carbon atoms and a saturated alcohol having 35–40 carbon atoms, and |
| 2.0–3.0% by weight | of water. |

It is preferred to select the ratio of beeswax and one or more esters of a saturated carboxylic acid having 20–40 carbon atoms and a saturated alcohol having 35–40 carbon atoms in a ratio of approximately 1:1 to approximately 1:5, in particular approximately 1:3.

The compositions according to the invention, which are used as emulsion lipstick bases, therefore contain a certain amount of water. It is possible, however, to dispense with an emulsifier since beeswax itself has emulsifying properties. However, it is advantageous and preferred to incorporate an emulsifier, in particular a water-in-oil emulsifier (W/O emulsifier).

Surprisingly, the polyglycerol fatty acid esters have proved to be particularly preferred W/O emulsifiers which lead to surprisingly stable and particularly skin-friendly cosmetic sticks which, moreover, result in cosmetically particularly elegant formulations. Polyglyceryl 3-diisostearate (synonym: triglyceryl diisostearate) is particularly advantageous.

The advantageous polyglycerol esters according to the invention and their occurrence, properties and use in cosmetics are listed and dealt with in the "Lexikon der Hilfsstoffe für Pharmazie, Kosmetik und angrenzende Gebiete" [Encyclopedia of auxiliaries for pharmacology, cosmetology and adjacent fields], H. P. Fiedler, 3rd Ed., 1989, Editio Cantor Aulendorf, and sources and cross-references cited therein under the head words "Polyglycerinester" [polyglycerol esters], "Polyglycerolester" [polyglycerol esters], "Polyglyceryl-3-diisostearate" [polyglyceryl 3-diisostearates], "Triglycerin" [triglycerol] and "Triglyceryldiisostearat" [triglyceryl diisostearate] and the like. The polyglycerol esters described therein are highly suitable for the present invention.

Thus, cosmetic sticks are characterised not only by a content of beeswax, octacosanyl stearate and water, but also by a content of one or more emulsifiers from amongst the group of the polyglycerol fatty acid esters, in particular polyglyceryl 3-diisostearate, according to the invention.

The emulsifiers can be incorporated advantageously into the compositions according to the invention in amounts of 0.05–10.0% by weight, in particular in amounts of 1.00–8.00% by weight, particularly preferably 2.00–4.00% by weight.

The customary ingredients of cosmetic sticks can advantageously be incorporated into the preparations according to the invention, i.e. waxes, in particular vegetable and/or animal waxes or chemically modified derivatives thereof, in particular carnauba wax, candelilla wax and the like, hydrocarbons, fats and oils for the matrix, and the conventional auxiliaries and additives, such as perfume oils, preservatives, pigments, light stabilizers and stabilizers.

Additionally, nutritive active substances can be incorporated which are not limited to the fat-soluble active substances, as has been the case to date, but which can also be selected from amongst the group of the water-soluble active substances, for example vitamins and the like.

It is particularly advantageous to select the remainder to 100% by weight, of the composition, from amongst the group of the following substances: glycerol tricarboxylic acid esters (synonym: triglycerides), Guerbet alcohols, myristyl myristate, jojoba oil and related substances. It is particularly advantageous to incorporate other liquid fatty components into the compositions according to the invention, for example fractionated coconut oils.

Again, additional auxiliaries and additives and active substances, in particular nutritive active substances, can be incorporated which are not limited to fat-soluble active substances, as has been the case to date, but which can also be selected from amongst the group of the water-soluble active substances, for example vitamins and the like.

Thus, compositions for cosmetic sticks containing
(a) beeswax,
(b) octacosanyl stearate and
(c) water
and substances selected from amongst the group of the
(d) glycerol tricarboxylic acid esters,
(e) Guerbet alcohols,
(f) myristyl myristate,
(g) jojoba oil and
(h) fractionated coconut oils,
and, if appropriate, additionally substances selected from amongst the group of the waxes, hydrocarbons, fats, oils, other auxiliaries and additives, such as perfume oils, preservatives, pigments, light stabilizers, stabilizers and fat- and/or water-soluble active substances, are also according to the invention.

For the abovementioned reasons it is, however, advantageous to entirely dispense with hydrocarbons. Nevertheless, the compositions according to the invention also result in extremely high-quality cosmetic sticks with advantageous properties even when used together with hydrocarbons.

The glycerol triesters can be selected advantageously from amongst the group of the so-called neobee oils and the fats. With regard to the state of the art of the glycerol triesters, their occurrence, properties and use in cosmetology, see "Lexikon der Hilfsstoffe für Pharmazie, Kosmetik und angrenzende Gebiete" [Encyclopedia of auxiliaries for pharmacology, cosmetology and adjacent fields], H. P. Fiedler, 3rd Ed., 1989, Editio Cantor Aulendorf, and sources and cross-references cited therein under the head word "Triglyceride" [triglycerides]. The triglycerides described therein are highly suitable for the present invention.

Guerbet alcohols are to be understood as meaning branched-chain alcohols of the general structure

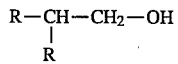

R preferably represents hydrocarbon radicals from $C_6$ to $C_{12}$ (for the state of the art of the preparation, properties and use of the Guerbet alcohols: "Lexikon der Hilfsstoffe für Pharmazie, Kosmetik und angrenzende Gebiete" [Encyclopedia of auxiliaries for pharmacology, cosmetology and adjacent fields], H. P. Fiedler, 3rd Ed., 1989, Editio Cantor Aulendorf, sources and cross-references cited therein under the head word "Guerbet-Alkohole" [Guerbet alcohols]).

Even though it is conceivable and can, if appropriate, also be advantageous to design sticks according to the present invention for purposes other than lipsticks, for example as deodorant sticks, it is expected that consumer acceptance in the fields of application in question is relatively poor since most of the compositions according to the invention leave a slightly oily sensation. In the case of a lipstick, this is perfectly desirable and very pleasant.

However, at least according to an assessment of the Central European consumer spectrum, non-oiliness is precisely what is expected from a deodorant stick.

The cosmetic sticks according to the invention can advantageously be produced by a process characterized in that
(1) beeswax and octacosanyl stearate and, if appropriate, one or more emulsifiers selected from amongst the group of the W/O emulsifiers, in particular the polyglycerol fatty acid esters, particularly advantageously polyglyceryl 3-diisostearate, and fatty components selected from amongst the group of the glycerol tricarboxylic acid esters, Guerbet alcohols, myristyl myristate, jojoba oil and/or related substances and the fractionated coconut oils are melted and, if appropriate, subjected to steps (2) and (3), i.e.
(2) water is added continuously until the desired water content of the cosmetic stick is achieved,
(3) the resulting mixture is stirred during the addition of water, and
(4) the uniform, stirred mixture is then introduced into moulds and allowed to cool slowly.

The examples which follow are intended to illustrate the present invention, but this is not intended to limit the present invention to these examples. Rather, there is a wide range of modifications, minor alterations and the like, which a person skilled in the art can carry out on the basis of his expert knowledge without having to leave the scope of the present invention. The individual substances employed are selected analogously to the CTFA nomenclature, with the exception of those substances which also have a simple chemical name (for example: water).

|  | % by weight |
|---|---|
| Example 1 |  |
| Caprylic/capric triglyceride | 25 |
| Octyldodecanol | 25 |
| Caprylic/capric diglyceryl succinate | 5 |
| Jojoba oil | 5 |
| Myristyl myristate | 10 |
| Octacosanyl stearate | 20 |
| White beeswax | 9 |
| Octyl metoxycinnamate | 1 |
| Example 2 |  |
| Octyldodecanol | 45 |
| Caprylic/capric diglyceryl succinate | 10 |
| Squalene | 7 |
| Jojoba oil | 3 |
| Myristyl myristate | 8 |
| Carnauba wax | 2 |
| Octacosanyl palmitate | 11 |
| Octacosanyl stearate | 4 |
| White beeswax | 10 |
| Example 3 |  |
| Cetyl palmitate | 8 |
| Squalene | 15 |
| Wheat germ oil | 5 |
| Propylene glycol dicaprylate/caproate | 10 |
| Caprylic/capric triglyceride | 10 |
| Octyldodecanol | 20 |
| Polyisobutene | 2 |
| Cyclomethicone | 10 |
| Hexacosanyl palmitate | 10 |
| Example 4 |  |
| White beeswax | 26 |
| Caprylic/capric diglyceryl succinate | 15 |
| Propylene glycol dicaprylate/dicaprate | 7 |
| Caprylic/capric triglyceride | 24 |
| Squalene | 10 |
| Shea butter | 7 |
| Octacosanyl stearate | 6 |
| Octyl methoxycinnamate | 5 |
| Example 5 |  |
| Caprylic/capric triglyceride | 14 |
| Octyldodecanol | 20 |
| Jojoba oil | 10 |
| Myristyl myristate | 10 |
| Octacosanyl stearate | 20 |
| Cetyl palmitate | 2 |
| White beeswax | 8 |
| Polyglyceryl 3-diisostearate | 4 |
| Glycine | 1 |
| $ZnSO_4 \cdot H_2O$ | 1 |
| Water (the pH is brought to 6–7 using | 10 |

| | % by weight |
|---|---|
| NaOH) | |
| Example 6 | |
| Caprylic/capric triglyceride | 20 |
| Octyldodecanol | 15 |
| Cetearyl alcohol | 5 |
| Shea butter | 10 |
| Jojoba oil | 8 |
| Polyglyceryl 3-diisostearate | 2 |
| Polyisobutene | 2 |
| Octacosanyl stearate | 10 |
| Cetyl palmitate | 5 |
| White beeswax | 10 |
| Glycerol | 3 |
| Wheat germ oil | 2 |
| Triacontanyl palmitate | 5 |
| Water | 3 |
| Example 7 | |
| Octyldodecanol | 42 |
| Caprylic/capric diglyceryl succinate | 5 |
| Squalene | 5 |
| Jojoba oil | 5 |
| Myristyl myristate | 8 |
| Octacosanyl stearate | 20 |
| White beeswax | 10 |
| Polyglyceryl 3-diisostearate | 2 |
| Water | 3 |
| Example 8 | |
| Caprylic/capric triglyceride | 25 |
| Octyldodecanol | 11 |
| Caprylic/capric diglyceryl succinate | 12.5 |
| Propylene glycol dicaprylate/dicaprate | 7 |
| White beeswax | 26 |
| Polyglyceryl 3-oleate | 3.5 |
| Octacosanyl palmitate | 5 |
| Water | 10 |
| Example 9 | |
| Jojoba oil | 4 |
| Myristyl myristate | 7 |
| Polyglyceryl 3-oleate | 4 |
| Glyceryl lanolate | 1.5 |
| Wool wax alcohol | 1 |
| Octacosanyl stearate | 5 |
| Ceresin | 15 |
| Caprylic/capric diglyceryl succinate | 12.5 |
| Propylene glycol dicaprylate/dicaproate | 7 |
| Caprylic/capric triglyceride | 2.5 |
| Octyldodecanol | 33 |
| Cetearyl alcohol | 0.5 |
| Tocopheryl acetate | 0.1 |
| Water | 4.9 |

EXAMPLE 10

The cosmetic sticks according to Examples 1–9 were assessed with the aid of subjective and objective evaluation criteria.

Subjective evaluation criteria were the sensation during applying (dull, smooth, oily, greasy, tacky), the visual impression (matt, shiny). In all cases, the cosmetic sticks according to the invention were distinguished by superior sensation during application and by outstanding visual impression.

Objective assessment criteria were resistance to breakage, material rub-off and penetration.

Compared with compositions of the prior art, the compositions according to the invention showed an improved resistance to breakage.

The material rub-off can be determined readily by drawing a stick along a substrate, using a defined pressure. Sticks having low material rub-off are considered as dry while sticks having high material rub-off are considered as greasy.

In comparison with compositions of the prior art, the material rub-off of the compositions according to the invention was improved. The material rub-off are within the range which is associated with a very pleasant sensation during use.

The penetration is determined by measuring the depth to which a pointed needle penetrates the lipstick composition. Compositions into which the needle hardly penetrates are considered as hard, while those into which the needle penetrates very readily are equally considered as slightly unpleasant since they are too soft.

In comparison with compositions of the prior art, the compositions according to the invention showed an improved penetration. The penetration values are within the range which is associated with a very pleasant sensation during use.

We claim:

1. A uniform composition for an emulsion cosmetic stick, by weight consisting of
   a) 0.5 to 50% beeswax,
   b) 0.5 to 50% of at least one ester of a saturated carboxylic acid and a saturated alcohol,
      ba) the acid having 10–19 carbon atoms and the alcohol 14–40 carbon atoms, or
      bb) the acid having 20–40 carbon atoms and the alcohol having 35–40 carbon atoms,
   c) 0.1 to 20% of water, and
   d) optionally one member selected from the group consisting of an emulsifier, perfume oil, pigment, light stabilizer, moisturizer, vitamin, and preservative
   the composition being substantially free of paraffins and the ratio of (a):(b) ranging from 1:1 to 1:5.

2. A composition according to claim 1, by weight consisting of
   a) 2–20%,
   b) 2–25%, and
   c) 0.1–10%.

3. A composition according to claim 1, by weight consisting of
   a) 3–10%,
   b) 5–20%, and
   c) 3–5%,
   the ratio of (a): (b) ranging from 1:1 to 1:5.

4. A composition according to claim 1, by weight consisting of
   a) 4–6%,
   b) 15–18%, and
   c) 2–3%,
   the ratio of (a): (b) being 1:3.

5. A composition according to claim 1, wherein (b) is selected from the group consisting of hexacosanyl palmitate, octacosanyl palmitate, triacontanyl palmitate, dotriacontanyl palmitate, tetratriacontanyl palmitate, hexacosanyl stearate, octacosanyl stearate, triacontanyl stearate, dotriacontanyl stearate and tetratriacontanyl stearate.

6. A composition according to claim 1, wherein (d) includes polyglyceryl fatty acid ester as an emulsifier.

7. A composition according to claim 1, wherein (d) includes polyglyceryl 3-diisostearate as an emulsifier.

8. A composition according to claim 1, wherein (b) comprises octacosanyl stearate and (d) includes at least one member selected from the group consisting of da) a glycerol tricarboxylic acid ester,
db) a Guerbet alcohol,
dc) myristyl myristate,
dd) jojoba oil, and
de) a fractionated coconut oil.

9. A composition according to claim 1, wherein (d) includes at least one polyglycerol fatty acid ester.

10. A composition according to claim 1, in the form of a lipstick of uniform composition, wherein (b) comprises octacosanyl stearate present in 1.3 times the molar amount of (a), (d) includes polyglyceryl 3-diisostearate as an emulsifier and (d) further includes at least one member selected from the group consisting of a perfume oil, pigment, or light stabilizer, stabilizer, moisturizer and a vitamin.

* * * * *